US010881337B2

(12) United States Patent
Dalene

(10) Patent No.: US 10,881,337 B2
(45) Date of Patent: Jan. 5, 2021

(54) SHIELDED, FOLDED CONNECTOR FOR A SENSOR

(71) Applicant: Edwards Lifesciences Corporation, Irvine, CA (US)

(72) Inventor: Matthew Dalene, Clinton, CT (US)

(73) Assignee: Edwards Lifesciences Corporation, Irvine, CA (US)

( * ) Notice: Subject to any disclaimer, the term of this patent is extended or adjusted under 35 U.S.C. 154(b) by 966 days.

(21) Appl. No.: 15/407,049

(22) Filed: Jan. 16, 2017

(65) Prior Publication Data
US 2017/0202495 A1 Jul. 20, 2017

Related U.S. Application Data

(60) Provisional application No. 62/279,470, filed on Jan. 15, 2016, provisional application No. 62/324,125, filed on Apr. 18, 2016.

(51) Int. Cl.
A61B 5/1455 (2006.01)
H05K 1/02 (2006.01)
H01R 12/77 (2011.01)
H01R 13/658 (2011.01)
H01R 13/66 (2006.01)
H01R 13/70 (2006.01)

(52) U.S. Cl.
CPC ......... A61B 5/14552 (2013.01); H01R 12/77 (2013.01); H01R 13/658 (2013.01);
(Continued)

(58) Field of Classification Search
CPC ............ A61B 5/14522; A61B 2562/12; A61B 2562/222; A61B 2562/227; H01R 12/77;
(Continued)

(56) References Cited

U.S. PATENT DOCUMENTS 4,026,011 A * 5/1977 Walton .................. H01R 12/62
29/846
4,714,435 A 12/1987 Stipanuk et al.
(Continued)

FOREIGN PATENT DOCUMENTS

JP 2002319750 A 10/2002

OTHER PUBLICATIONS

Markus Wille, "Basic Designs of Flex-Rigid Printed Circuit Boards", PCB Fabrication, OnBoard Technology, Jun. 2006, pp. 8-13.
(Continued)

Primary Examiner — Jacqueline Cheng
Assistant Examiner — Tho Q Tran
(74) Attorney, Agent, or Firm — Getz Balich LLC

(57) ABSTRACT

An oximetry sensor assembly connector, and a method for making the same, is provided that includes a flexible circuit and a stiffener panel. The flexible circuit has a plurality of layers including at least one electrical trace layer and at least one electromagnetic interference (EMI) shield layer. The stiffener panel has a first side surface and a second side surface, which second side surface is opposite the first side surface. The flexible circuit includes a first segment and a second segment, and one or more of the plurality of layers are disposed within the first segment and the second segment. The flexible circuit is folded such that the first segment is contiguous with the first side surface of the stiffener panel, and the second segment is contiguous with the second side surface of the stiffener panel.

12 Claims, 15 Drawing Sheets

(52) U.S. Cl.
CPC ............ *H01R 13/665* (2013.01); *H01R 13/70* (2013.01); *H05K 1/028* (2013.01); *H05K 1/0216* (2013.01); *H05K 1/0219* (2013.01); *H05K 1/0274* (2013.01); *A61B 2562/12* (2013.01); *A61B 2562/222* (2013.01); *A61B 2562/227* (2013.01); *H05K 2201/056* (2013.01); *H05K 2201/0723* (2013.01); *H05K 2201/09727* (2013.01)

(58) Field of Classification Search
CPC .... H01R 13/658; H01R 13/665; H01R 13/70; H05K 1/0216; H05K 1/0274; H05K 1/028; H05K 2201/056; H05K 2201/0723; H05K 2201/09727; H05K 1/0219

See application file for complete search history.

(56) References Cited

U.S. PATENT DOCUMENTS

| | | | |
|---|---|---|---|
| 4,815,990 A * | 3/1989 | Ristedt | H01R 12/61 |
| | | | 29/846 |
| 5,678,544 A | 10/1997 | DeLonzor | |
| D393,830 S | 4/1998 | Tobler | |
| 6,745,061 B1 * | 6/2004 | Hicks | A61B 5/14552 |
| | | | 600/323 |
| 6,934,570 B2 | 8/2005 | Kiani | |
| 7,072,701 B2 | 7/2006 | Chen et al. | |
| 7,272,425 B2 | 9/2007 | Al-Ali | |
| 7,340,287 B2 * | 3/2008 | Mason | A61B 5/14552 |
| | | | 600/344 |
| 7,341,559 B2 | 3/2008 | Schulz | |
| 8,396,526 B2 | 3/2013 | Benni | |
| 2003/0150631 A1 * | 8/2003 | Yamada | H05K 1/0218 |
| | | | 174/354 |
| 2005/0012199 A1 | 1/2005 | Rosenau et al. | |
| 2005/0283059 A1 * | 12/2005 | Iyer | A61B 5/14542 |
| | | | 600/338 |
| 2014/0051956 A1 | 2/2014 | Dalene et al. | |
| 2014/0171761 A1 | 6/2014 | Dalene | |
| 2015/0099951 A1 | 4/2015 | Al-Ali | |

OTHER PUBLICATIONS

International search report for PCT/US2017/013654 dated Apr. 5, 2017.

* cited by examiner

SHIELDED, FOLDED CONNECTOR FOR A SENSOR

This application claims priority to U.S. Patent Appln. No. 62/279,470 filed Jan. 15, 2016 and U.S. Patent Appln. No. 62/324,125 filed Apr. 18, 2016, which applications are hereby incorporated by reference in their entireties.

BACKGROUND OF THE INVENTION

Technical Field

The present application relates to spectrophotometric sensors in general, and to connectors that may be used with spectrophotometric sensors in particular.

Background Information

Sensor assemblies, such as near-infrared spectroscopy (NIRS) sensor assemblies, are commonly used to non-invasively measure a characteristic (e.g., blood oxygenation) of a biological tissue. For example, United States patent application publication number 2014/0171761, the contents of which are incorporated herein by reference, describes an application environment that includes one or more light sources, one or more light detectors, insulating layers, shielding layers, and a connector incorporated as part of a flexible/flex circuit design configuration.

Some prior art sensor connectors comprise multiple layers; e.g., circuitry layers, insulation layers, and stiffener layers. A typical stiffener is an "FR-4" (which is a grade designation) composite material composed of woven fiberglass cloth with an epoxy resin binder that is flame resistant or self-extinguishing.

There are several issues associated with prior art multiple layer composite connectors. For example, alignment between layers is critical. Errors in alignment can create a defective connector. The tooling necessary to attain the required precision increases the sensor connector manufacturing cost. The stiffeners layer(s) are often formed by cutting or stamping the desired stiffener geometry from a sheet of material (e.g., FR-4). Because of the geometry of the layer(s), only a limited number of parts can be cut from the sheet material. The process therefore creates an undesirable amount of waste, and increases the cost of manufacturing the sensor. Furthermore, the stiffener geometries are often formed with rough edges. If the rough edges are not deburred or otherwise smoothed (which would be an additional manufacturing step), the edges can cause premature wear within mating connector parts, and/or debris within the connector parts.

SUMMARY OF THE INVENTION

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the present disclosure are directed to an oximetry sensor assembly connector. The connector includes a flexible circuit and a stiffener panel. The flexible circuit has a plurality of layers including at least one electrical trace layer and at least one electromagnetic interference (EMI) shield layer. The stiffener panel has a first side surface and a second side surface, which second side surface is opposite the first side surface. The flexible circuit includes a first segment and a second segment, and one or more of the plurality of layers are disposed within the first segment and the second segment. The flexible circuit is folded such that the first segment is contiguous with the first side surface of the stiffener panel, and the second segment is contiguous with the second side surface of the stiffener panel.

According to another aspect of the present disclosure, an oximetry sensor assembly is provided that includes at least one light source, at least one light detector, a flexible circuit, and a connector. The flexible circuit has a plurality of layers including at least one electrical trace layer and at least one electromagnetic interference (EMI) shield layer. The connector that includes a stiffener panel having a first side surface and a second side surface, which second side surface is opposite the first side surface. The flexible circuit extends between the light source and light detector proximate a first end, and the connector at a second end opposite the first end. The flexible circuit includes a first segment and a second segment, and one or more of the plurality of layers are disposed within the first segment and the second segment. The flexible circuit is folded such that the first segment is contiguous with the first side surface of the stiffener panel, and the second segment is contiguous with the second side surface of the stiffener panel.

According to another aspect of the present disclosure, a method of manufacturing a sensor assembly is provided. The method includes: a) providing a flexible circuit having a plurality of layers including at least one electrical trace layer and at least one electromagnetic interference (EMI) shield layer, wherein the flexible circuit includes a first segment and a second segment, and one or more of said plurality of layers are disposed within the first segment and the second segment; b) providing a stiffener panel having a first side surface, a second side surface, and an insertion edge, which second side surface is opposite the first side surface; and c) folding the flexible circuit around the insertion edge so that the first segment is contiguous with and attached to the first side surface of the stiffener panel, and the second segment is contiguous with and attached to the second side surface of the stiffener panel.

In some embodiments of any of the above described aspects, the stiffener panel includes an insertion edge that extends between the first side surface and the second side surface, and the flexible circuit is folded around the insertion edge.

In some embodiments of any of the above described aspects and embodiments, the first segment of the flexible circuit includes a first exposed portion adjacent the insertion edge of the stiffener panel, and a first covered portion, and the second segment of the flexible circuit includes a second exposed portion adjacent the insertion edge of the stiffener panel, and a second covered portion.

In some embodiments of any of the above described aspects and embodiments, the plurality of layers within the flexible circuit includes a first electrically conductive layer and the first electrically conductive layer is exposed as the outermost layer in both the first exposed section and in the second exposed section.

In some embodiments of any of the above described aspects and embodiments, within the first exposed section, the plurality of layers of the flexible circuit includes in stacked order in a direction toward the stiffener panel, the first electrically conductive layer, a first electrically insulative layer, a second electrically conductive layer, a second electrically insulative layer, the EMI shield layer, and a cover layer, which cover layer is in contact with the first side surface of the stiffener panel.

In some embodiments of any of the above described aspects and embodiments, within the second exposed section, the plurality of layers of the flexible circuit includes in stacked order in a direction toward the stiffener panel, the first electrically conductive layer, the first electrically insulative layer, the second electrically conductive layer, the second electrically insulative layer, the EMI shield layer, and the cover layer, which cover layer is in contact with the second side surface of the stiffener panel.

In some embodiments of any of the above described aspects and embodiments, within the first covered portion of the first segment, the plurality of layers of the flexible circuit further includes a second cover layer in contact with the first electrically conductive layer, and within the second covered portion of the second segment, the plurality of layers of the flexible circuit further includes the second cover layer in contact with the first electrically conductive layer.

In some embodiments of any of the above described aspects and embodiments, the first electrically conductive layer includes one or more light source traces configured to conduct electrical signals between one or more light sources within the sensor assembly and one or both of the first and second exposed sections, and one or more EMI shield traces.

In some embodiments of any of the above described aspects and embodiments, the second electrically conductive layer includes one or more detector traces configured to conduct electrical signals between one or more light detectors within the sensor assembly and one or both of the first and second exposed sections, and one or more EMI shield traces.

In some embodiments of any of the above described aspects and embodiments, within the flexible circuit, one or more of the EMI shield traces in the second electrically conductive layer are aligned with the one or more light source traces within the first electrically conductive layer, and one or more of the EMI shield traces in the first electrically conductive layer are aligned with the one or more detector traces within the second electrically conductive layer.

In some embodiments of any of the above described aspects and embodiments, the stiffener panel includes a well extending between the first side surface and the second side surface, and further including one or more electrical components disposed within the well and in connection with the flexible circuit.

BRIEF DESCRIPTION OF THE DRAWINGS

The present disclosure is illustrated by way of example and not limited in the accompanying figures in which like reference numerals indicate similar elements.

DETAILED DESCRIPTION

Figure 1:
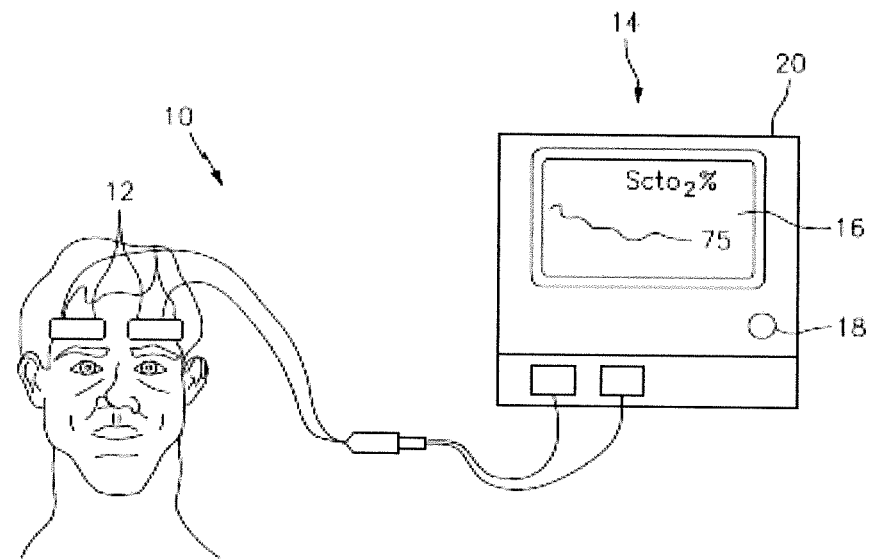
FIG. 1 is a diagrammatic view of a pair of sensor assemblies mounted on a patient and connected to a base unit.

It is noted that various connections are set forth between elements in the following description and in the drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities.

Figure 2:
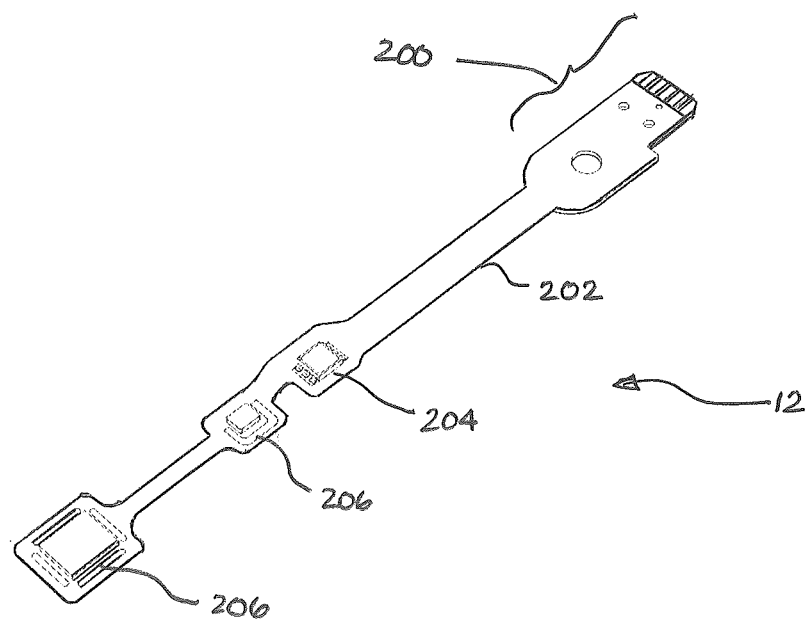
FIG. 2 is a top view of a sensor including a connector embodiment according to the present invention, shown in a configured for use state.
Figure 3:
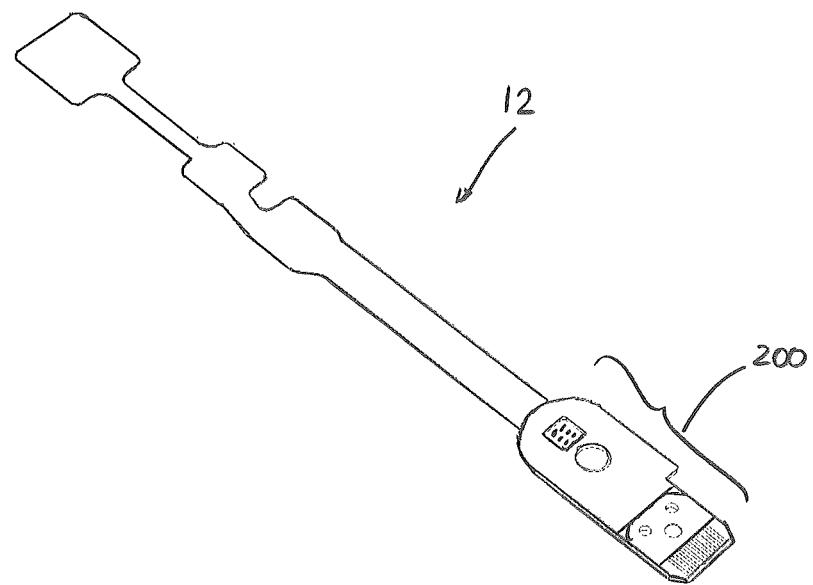
FIG. 3 is a bottom view of the sensor embodiment shown in FIG. 2.

Referring to FIGS. 1-3, a system 10 includes one or more sensor assemblies 12 (referred to hereinafter as "sensors") connected to a base unit 14. The base unit 14 includes a display 16, operator controls 18, and a processor 20 for providing signals to and/or receiving signals from each sensor 12. The processor 20 is configured (e.g., programmed) to selectively perform the functions necessary to operate each sensor 12; e.g., controlling light sources 204 (e.g. LEDs) within the sensor 12 to selectively produce light, and controlling light detectors 206 (e.g., photodiodes) to receive signals representative of sensed light emitted from light source 204 disposed within the sensor 12. The functionality of the processor 20 may be implemented using hardware, software, firmware, or a combination thereof. U.S. Pat. Nos. 7,072,701 and 8,396,526, both of which are hereby incorporated by reference in their entirety, describe non-limiting examples of oximetry systems that like that described above.

FIGS. 2 and 3 illustrate top and bottom views of an exemplary sensor 12 in an assembled (i.e., ready to use) configuration having a connector 200 embodiment according to the present invention. The sensor 12 includes a flexible circuit 202, a light source 204, and light detectors 206. As will be described below, the flexible circuit 202 electrically connects the light source 204 to the connector 200 and the light detectors 206 to the connector 200.

Figure 4:
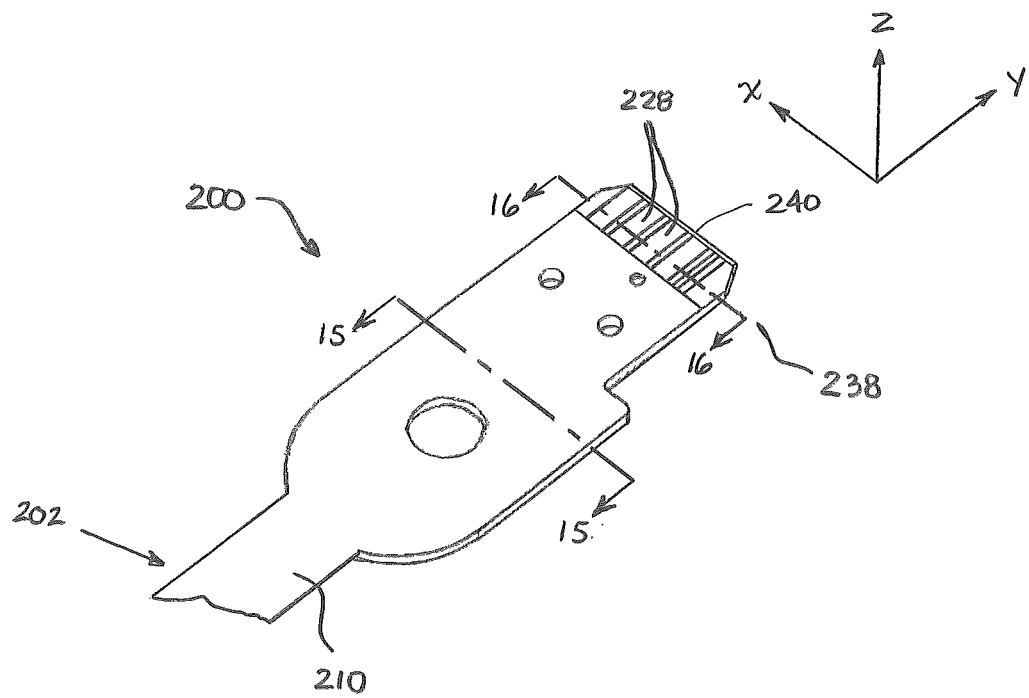
FIG. 4 is an enlarged portion of the top view shown in FIG. 2, showing the connector portion of the sensor.
Figure 5:
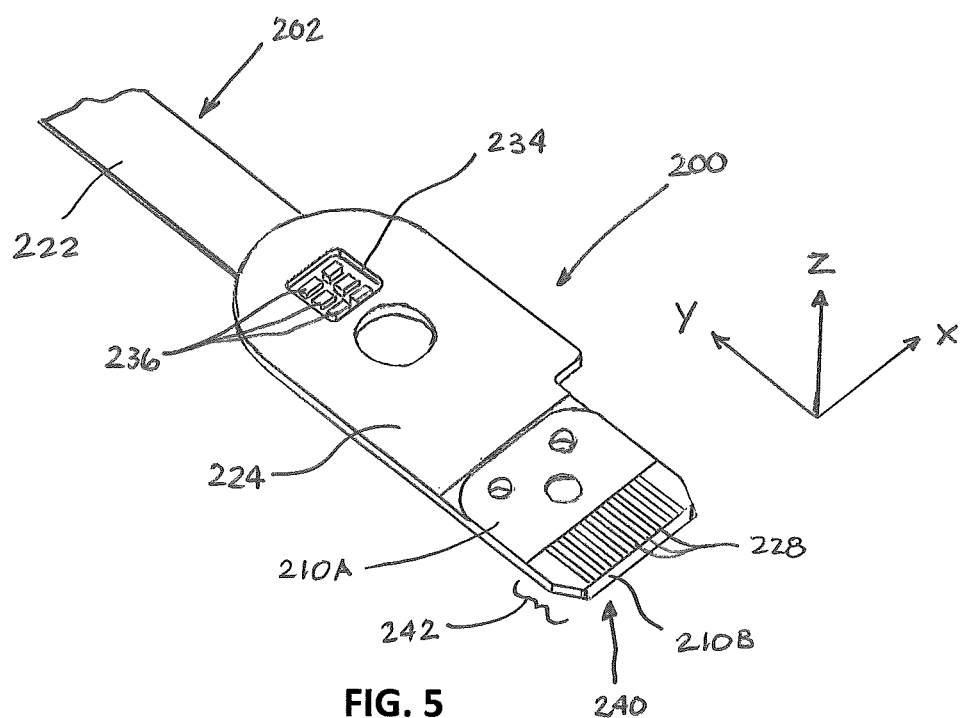
FIG. 5 is an enlarged portion of the bottom view shown in FIG. 3, showing the connector portion of the sensor.
Figure 18:
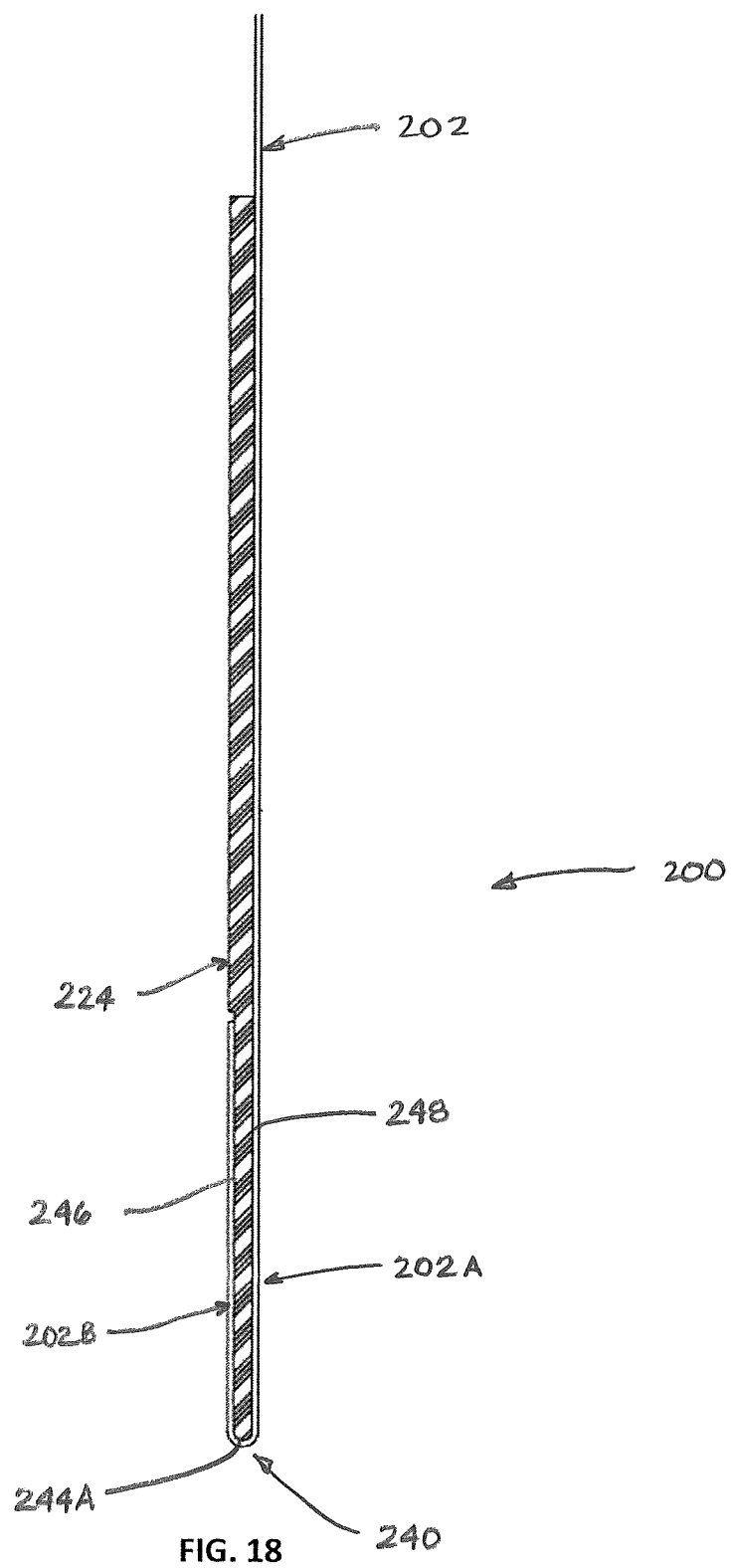
FIG. 18 is a diagrammatic side view of a connector embodiment.

FIGS. 4 and 5 illustrate enlarged top and bottom views of the connector 200 portion of the sensor 12 shown in FIGS. 2 and 3. The connector 200 may be described as having a width that extends along an X-axis, a length that extends along a Y-axis, and a thickness that extends along a Z-axis. At least a portion of the connector 200 is composed of the flexible circuit 202. As will be described below, the flexible circuit 202 is configured to fold substantially about a widthwise extending axis (referred to as the "fold axis" 208; e.g., see FIGS. 6A, 6B, 8, 9A, 10A, 11, 12, and 13). FIGS. 4, 5, and 18 illustrate the connector 200 in the assembled state (i.e., configured for use), in which state a portion of the flexible circuit 202 is folded. FIG. 18 shows a side view of the connector 200, illustrating the flexible circuit 202 folded around the insertion edge 244A of the stiffener panel 224; i.e., a first segment 202A of the flexible circuit 202 is disposed contiguous with and attached to the top side surface 248 of the stiffener panel 224 and a second segment 202B of the flexible circuit 202 is disposed contiguous with and attached to the bottom side surface 246 of the stiffener panel 224.

Figures 6A, 6B:
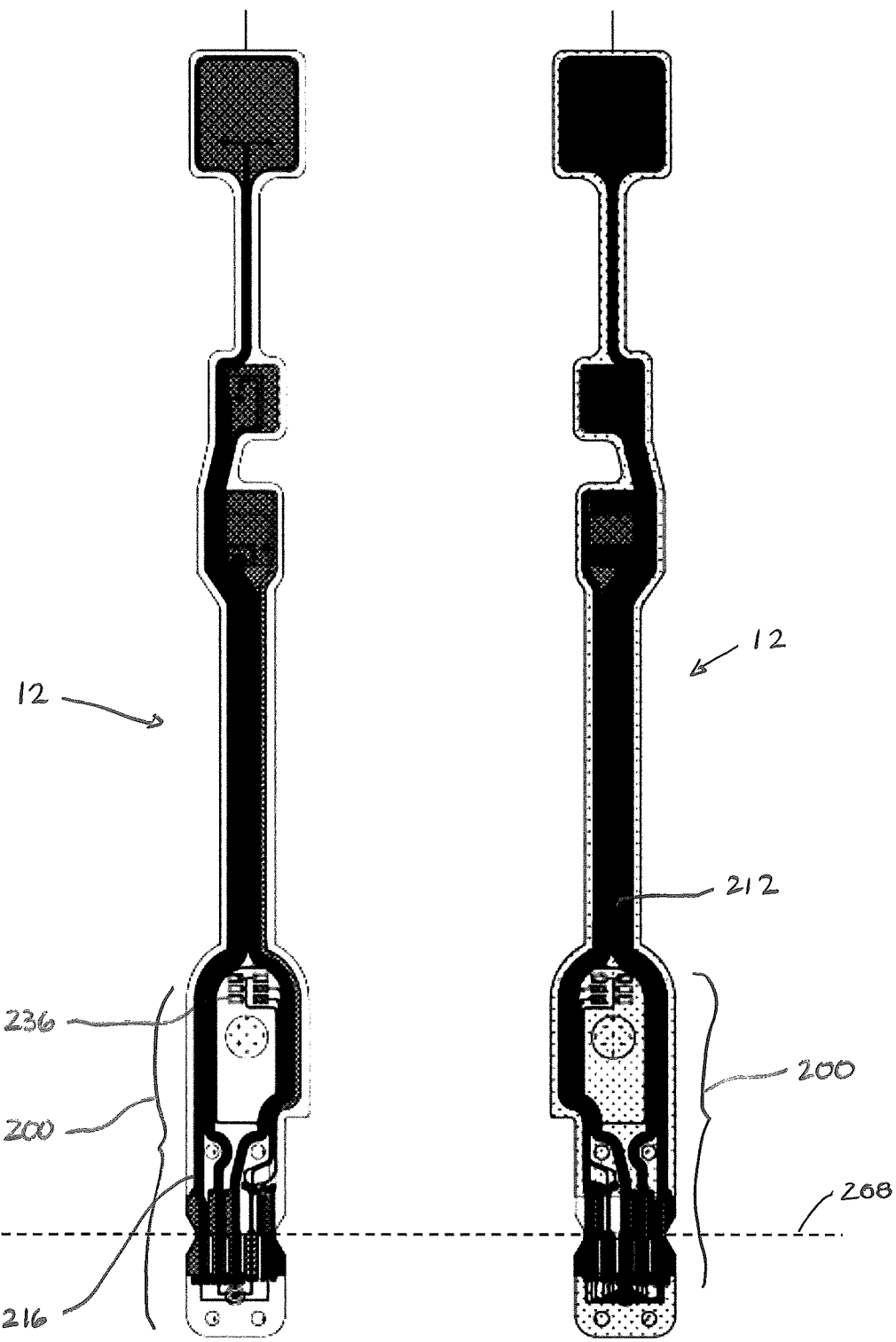
FIG. 6A is a diagrammatic planar view showing constituent layers of the flexible circuit sensor shown from a bottom side perspective.
FIG. 6B is a diagrammatic planar view showing constituent layers of the flexible circuit sensor shown from a top side perspective.

The flexible circuit 202 portion of the present connector includes a plurality of layers that are combined to form a single structure. The specific number and types of layers can vary to suit the particular application. A non-limiting exemplary embodiment of the connector flexible circuit layers is provided hereinafter for illustrative purposes. FIG. 6A is a diagrammatic planar view showing constituent layers of the flexible circuit 202 within the sensor 12 shown from a bottom side perspective. FIG. 6B is a diagrammatic planar view showing constituent layers of the flexible circuit 202 within the sensor 12 shown from a top side perspective. In both FIGS. 6A and 6B, the flexible circuit 202 is shown in an unfolded configuration. As will be described below, portions of the flexible circuit 202 are folded about the fold axis 208 during manufacture of the connector portion of the sensor.

Figure 7:
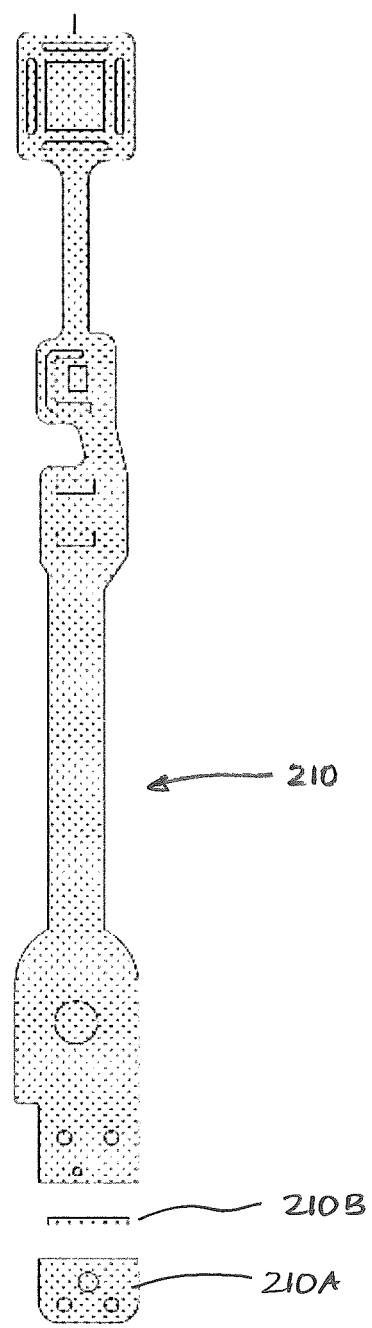
FIG. 7 is a planar view of a top cover layer embodiment.
Figure 8:
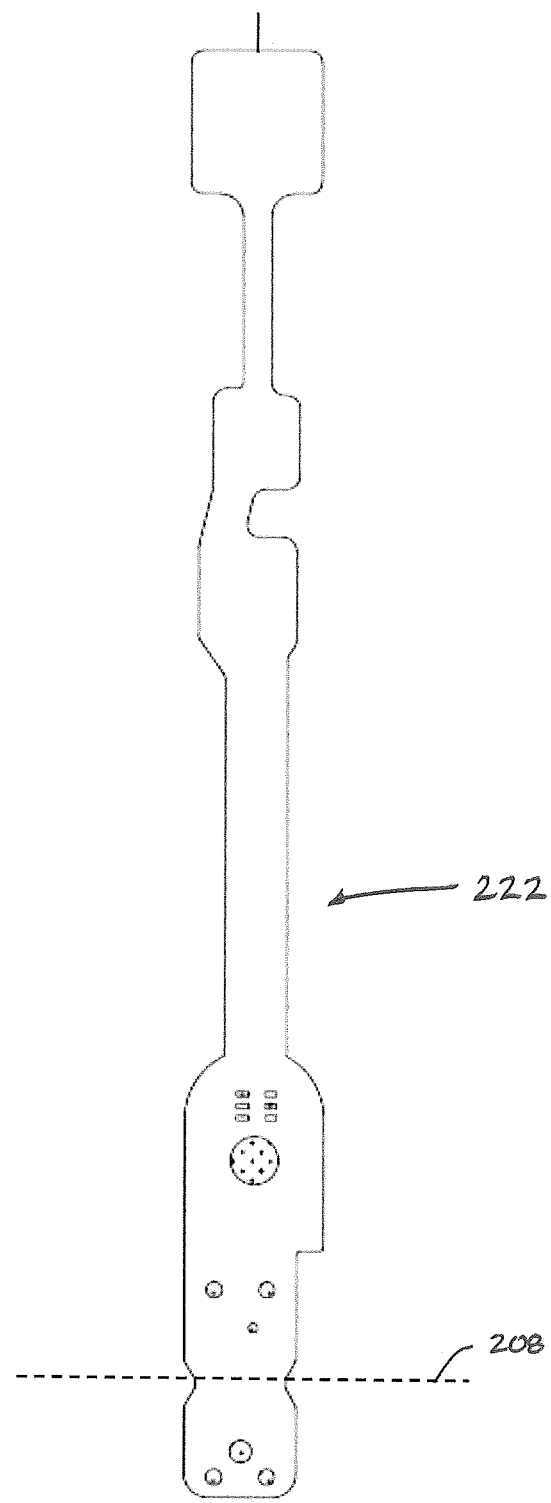
FIG. 8 is a planar view of a bottom cover layer embodiment.

In an exemplary embodiment, the flexible circuit 202 portion of the connector includes a plurality of layers (e.g., see FIGS. 7-13), including: top cover layer 210 (FIG. 7), a top electrical trace layer 212 (FIGS. 9 and 9A), a first electrically insulative layer 214 (FIG. 11), a bottom electrical trace layer 216 (FIGS. 10 and 10A), a second electrically insulative layer 218 (FIG. 12), an electromagnetic interference ("EMI") shield layer 220 (FIG. 13), and a bottom cover layer 222 (FIG. 8). The connector 200 further includes a stiffener panel 224 (e.g., see FIGS. 14, 14A, 14B).

Now referring to FIGS. 7 and 8, the top cover layer 210 (FIG. 7) and the bottom cover layer 222 (FIG. 8) may be formed of an electrically insulative material. A non-limiting example of an acceptable material is a polyamide polymer film (e.g., Kapton® polyamide film produced by E.I. du Pont de Nemours and Company—"DuPont"). As will be described below, the top and bottom cover layers 210, 222 are dimensioned to cover the respective electrical trace layers 212, 216 disposed within the connector 200. As can be seen in FIG. 7, the top cover layer 210 includes a separated segment 210A that is independent of the remainder of the top cover layer 210. In some embodiments, the top cover layer 210 may also include a second separated segment 210B that is disposed at the insertion end 240 of the assembled connector 200. The fold axis 208 shown in FIG. 8 illustrates the point at which the bottom cover layer 222 is folded over in the assembled sensor connector 200.

As can be seen in FIGS. 9, 9A, 10, and 10A, the top electrical trace layer 212 (FIGS. 9 and 9A) and the bottom electrical trace layer 216 (FIGS. 10 and 10A) include electrically conductive members (which may be referred to as "traces" or "wires"), some of which are configured to conduct electrical signals relative to electrical components within the sensor (e.g., the light source(s) 204, the light detector(s), memory devices, etc.) and some of which are configured to provide EMI shielding. The specific number of traces 228 within the top and bottom electrical trace layers 212, 216 can vary depending on the number of electrical components disposed within the sensor assembly 12. The traces 228 within the top and bottom electrical trace layers 212, 216 may be formed from an electrically conductive material such as copper, or an electrically conductive polymer, etc. Alternatively, the traces 228 may be formed from a first material that is coated with a second material that is electrically conductive. Still further, the traces 228 may be formed of a first material and coated (e.g. plated) with one or more second materials, all of which are electrically conductive. The term "electrically conductive" as used herein describes a material that is adequate to conduct electrical signals of the type and power necessary to conduct electrical signals to and from components within the sensor with an acceptably low level of resistance and/or interference.

Figure 9:
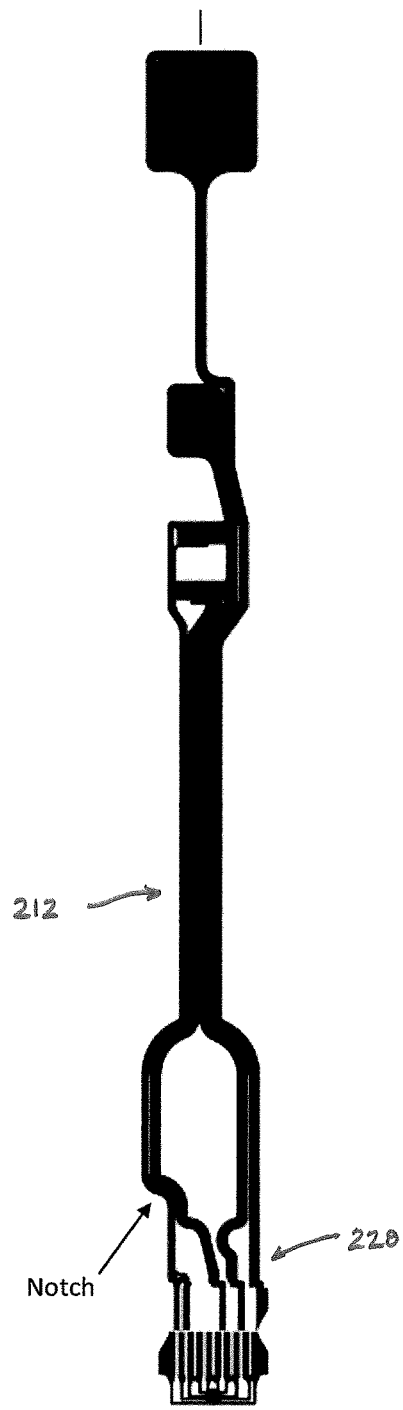
FIG. 9 is a planar view of a top electrical trace layer embodiment.
Figure 9A:
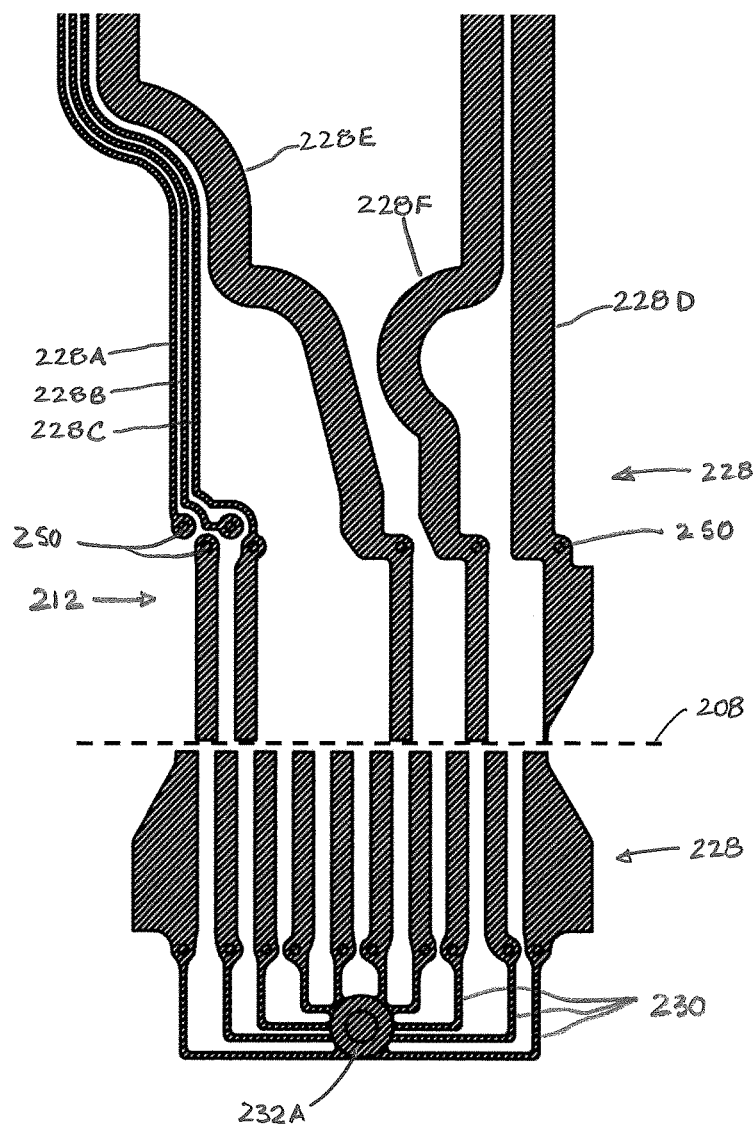
FIG. 9A is an enlarged portion of the top electrical trace layer embodiment shown in FIG. 9, showing the connector portion of the top electrical trace layer.

In the embodiment shown in FIGS. 9 and 9A, the top electrical trace layer 212 includes some traces (e.g., 228A, 228B, 228C) configured to conduct electrical signals relative to the light source(s) 204 (e.g., LEDs) disposed within the sensor 12. The top electrical trace layer further includes traces (e.g., 228D, 228E, 228F) that are configured to provide EMI shielding. These shielding traces are operable to conduct electrical energy generated by EMI signals; e.g., to a ground.

Figure 10:
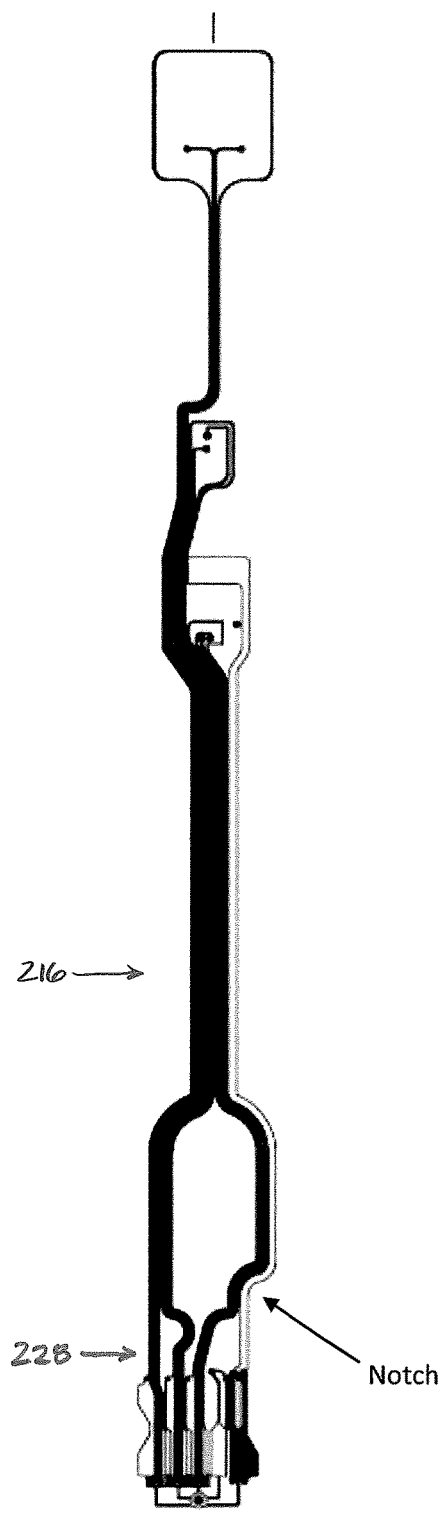
FIG. 10 is a planar view of a bottom electrical trace layer.
Figure 10A:
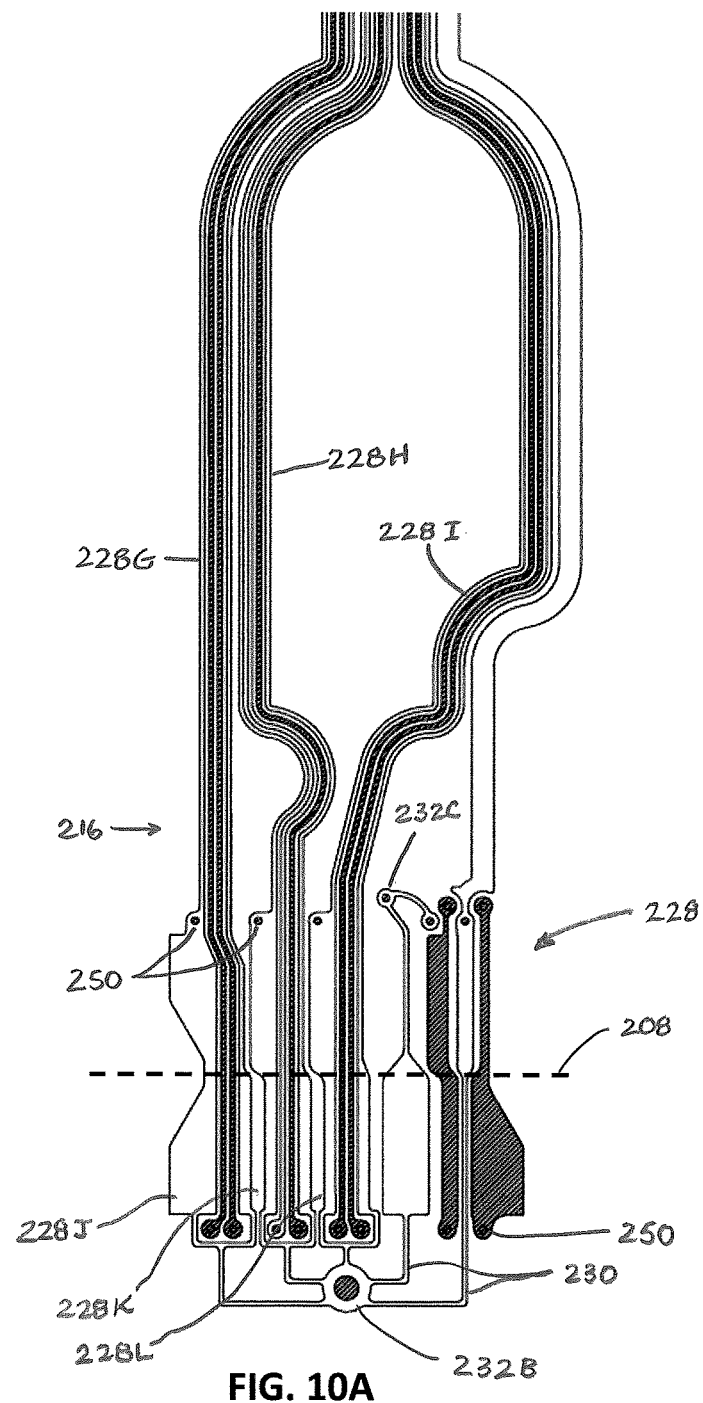
FIG. 10A is an enlarged portion of the top electrical trace layer embodiment shown in FIG. 10, showing the connector portion of the bottom electrical trace layer.

In the embodiment shown in FIGS. 10 and 10A, the bottom electrical trace layer 216 includes some traces (e.g., 228G, 228H, 228I) configured to conduct electrical signals relative to the light detector(s) 206 (e.g., photodiodes) disposed within the sensor 12. The bottom electrical trace layer 216 further includes some traces (e.g., 228J, 228K, 228L) configured to provide EMI shielding. These shielding traces are configured to conduct electrical energy generated by EMI signals; e.g., to a ground.

Figure 15:
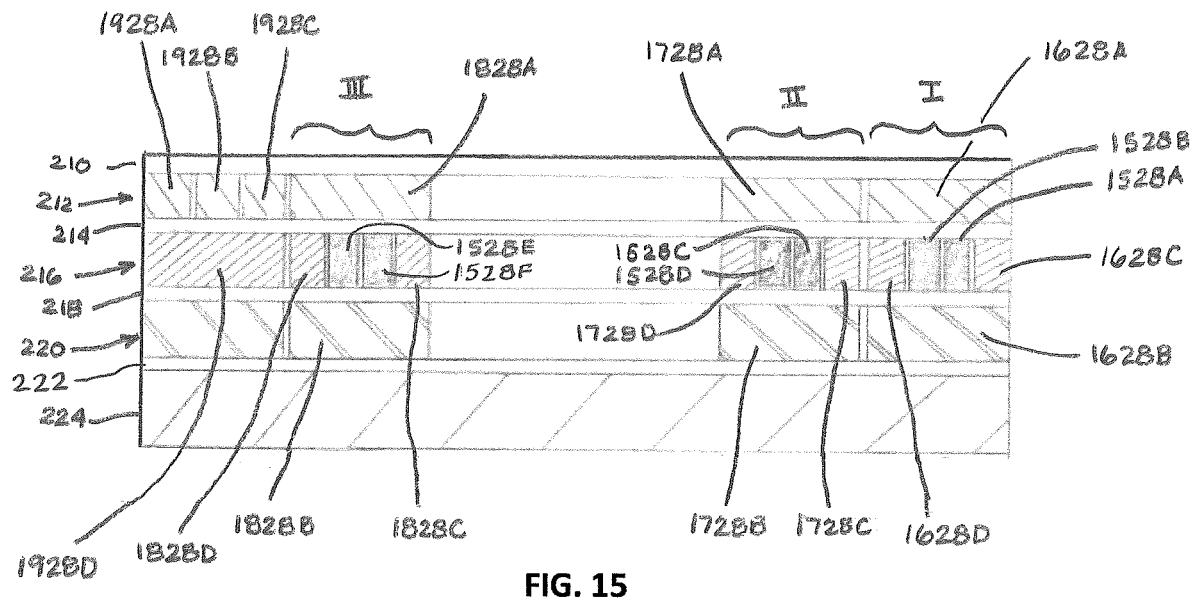
FIG. 15 illustrates a diagrammatic cross-section of a stack-up of layers within a flexible circuit embodiment, at the cross-section position 15-15 shown in FIG. 4.
Figure 16:
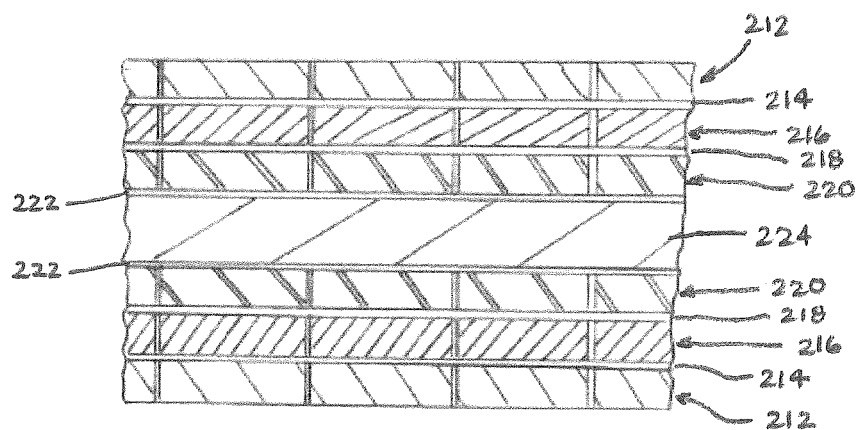
FIG. 16 illustrates a diagrammatic cross-section of a stack-up of layers within a flexible circuit embodiment, at the cross-section position 16-16 shown in FIG. 4.

At least some of the traces 228 within the top and bottom electrical trace layers 212, 216 are routed within the connector 200 to "align" with one another when the layers are assembled (i.e., "stacked"), as will be described below. The alignment between trace layers 212, 216 may vary at different (e.g., lengthwise or widthwise) locations within the connector 200. FIGS. 15 and 16 provide diagrammatic cross-sectional views of the connector 200 taken at different lengthwise positions to illustrate relative positioning or layers; e.g., how traces are positioned to align with one another at specific lengthwise positions of the connector 200.

It should be noted that FIGS. 9 and 10 show the top electrical trace layer 212 and the bottom electrical trace layer 216 in opposite orientations so that elements within the respective trace layers 212, 216 can be shown for description purposes. When assembled, the top and bottom electrical trace layers 212, 216 assume the same orientation; i.e., the bottom electrical trace layer 216 is rotated 180° from the orientation shown in FIGS. 10 and 10A. For example, when the top and bottom electrical trace layers 212, 216 are properly stacked within the flexible circuit 202, the "notch" feature (identified within FIGS. 9 and 10) of one trace layer is aligned with the other "notch" feature of the other trace layer. In the stacked configuration, the traces (e.g., 228G, 228H, 228I) within the bottom electrical trace layer 216 that extend through the flexible circuit 202 to the light detectors 206 are aligned with the shielding traces (e.g., 228D, 228E, 228F) within the top electrical trace layer 212.

In some embodiments, one or both of the top electrical trace layer 212 and the bottom electrical trace layer 216 may include trace extensions 230 routed to one or more common junctions 232A, 232B, 232C to facilitate manufacture of the respective trace layer. For example, the top electrical trace layer 212 embodiment shown in FIGS. 9 and 9A, includes trace extensions 230 that join one another at a junction 232A. Similarly, the bottom electrical trace layer 216 embodiment shown in FIGS. 10 and 10A includes trace extensions 230 that join one another at a junction 232B, and other traces at 232C. Extending the traces 230 to a common junction 232A, 232B enables the use of fewer electrical connections during the manufacturing process (e.g., during plating), thereby facilitating the manufacturing process. Moreover, in some embodiments as indicated above a plating of conductive material (e.g., gold) may be applied to the traces 228 (e.g., formed from copper) to increase the conductivity of the traces 228. At some point in the assembly of the sensor 12, the common junction 232A, 232B, 232C is removed (the trace extensions 230 may also be removed), thereby eliminating the physical and electrical connection between the traces 228 within the respective trace layer 212, 216.

Figure 11:
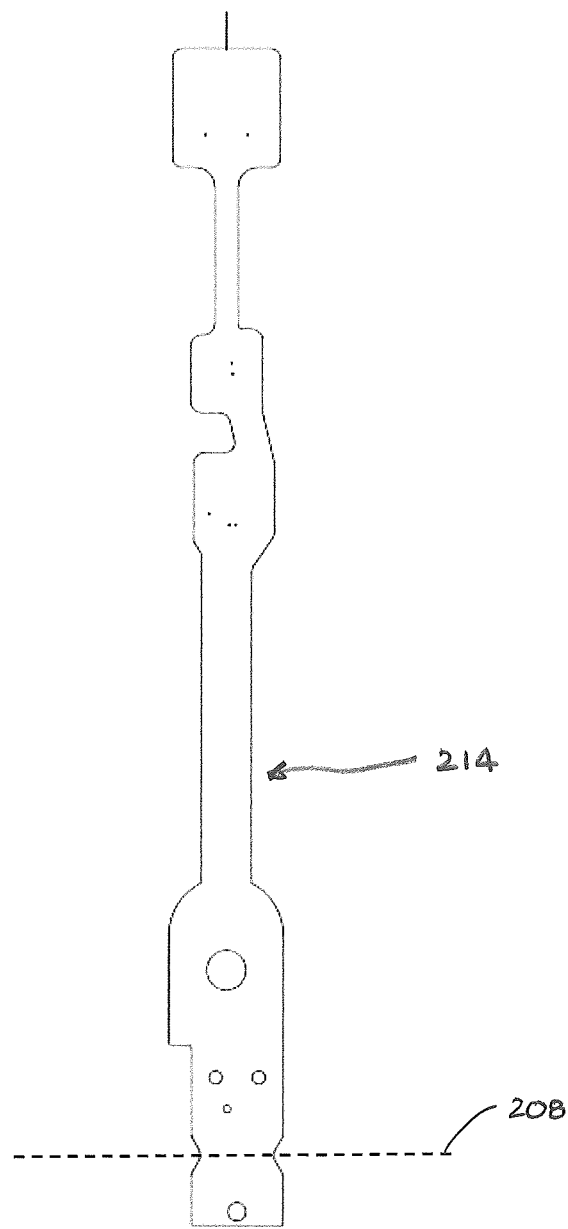
FIG. 11 is a planar view of a first electrically insulative layer embodiment.

Referring to FIG. 11, the first electrically insulative layer 214 is formed of an electrically insulative material, typically dimensioned to cover the respective plurality of electrical traces disposed within the connector. A non-limiting example of an acceptable material for the first electrically insulative layer 214 is a polyamide polymer film (e.g., Kapton® polyamide film produced by DuPont). The fold axis 208 shown in FIG. 11 illustrates the point at which the first electrically insulative layer 214 is folded over in the assembled sensor connector 200.

Figure 12:
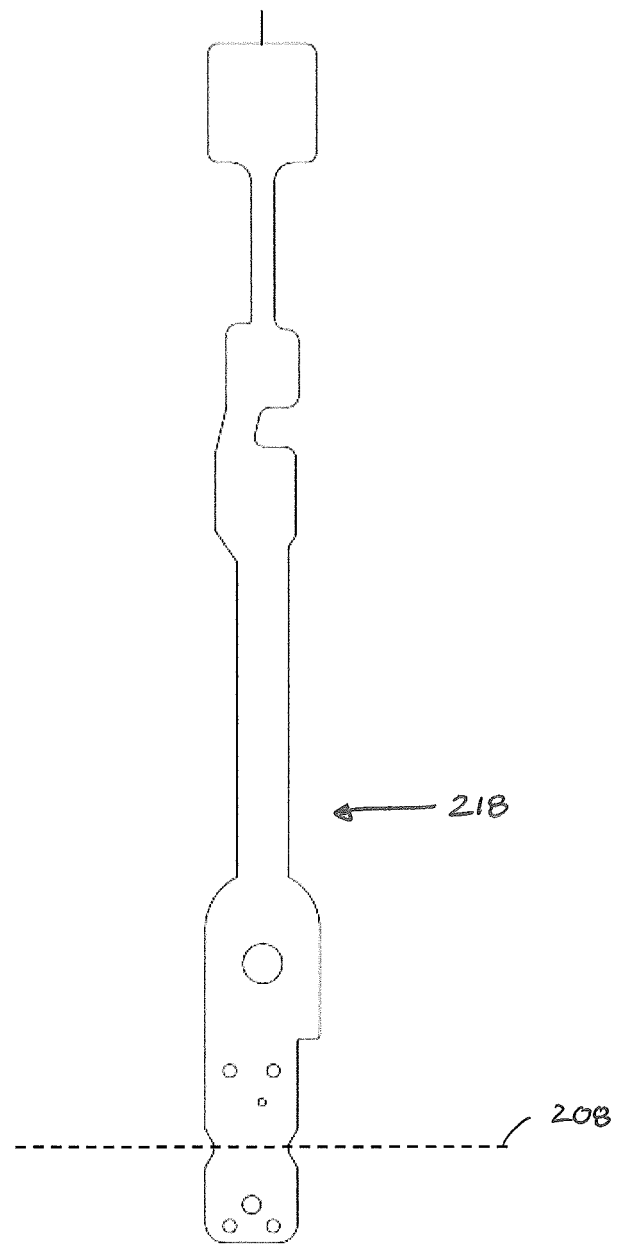
FIG. 12 is a planar view of a second electrically insulative layer embodiment.

Now referring to FIG. 12, the second electrically insulative layer 218 includes an electrically insulative substrate. Preferably, an adhesive material is adhered to one or both planar surfaces of the substrate (i.e., the widthwise extending non-edge surfaces). The adhesive material facilitates the assembly of the constituent flexible circuit layers during sensor 12 manufacturing. A non-limiting example of an acceptable electrically insulative substrate is a polyamide film material. The second electrically insulative layer 218 may be described as being an adhesive coated film tape. A non-limiting example of a commercially available adhesive coated film tape is FRO100, which is an adhesive polyamide film tape produced by DuPont. The fold axis 208 shown in FIG. 12 illustrates the point at which the second electrically insulative layer 218 is folded over in the assembled sensor connector 200.

Figure 13:
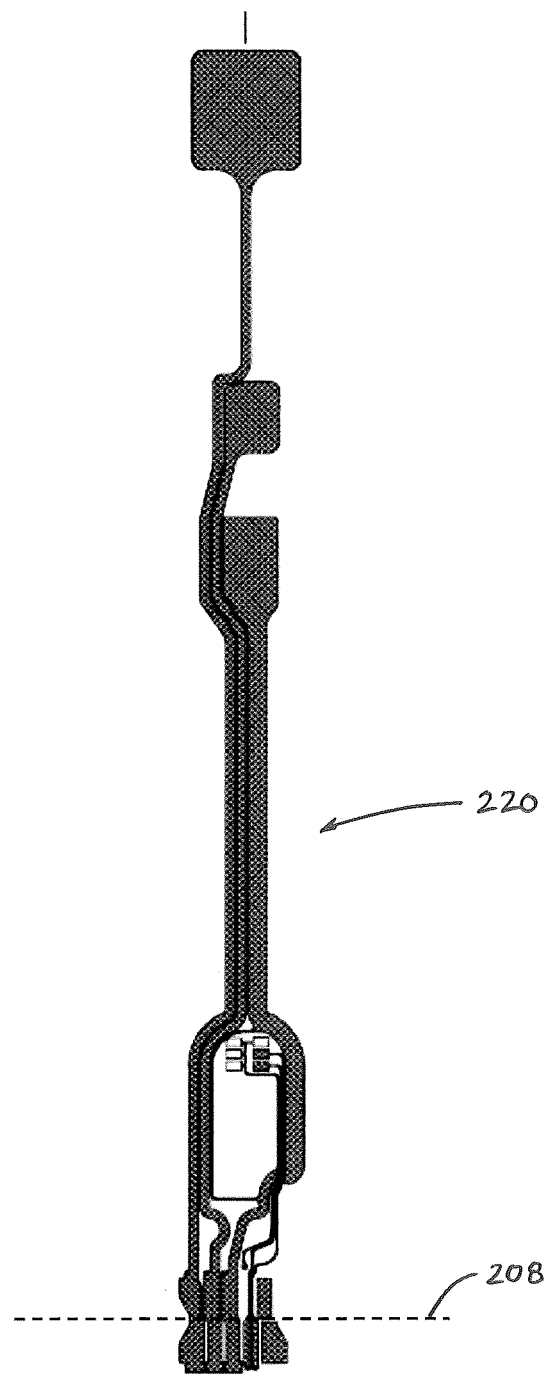
FIG. 13 is a planar view of an EMI shield layer embodiment, also illustrating sensor assembly components.

Now referring to FIG. 13, the EMI shield layer 220 is an electrically conductive material (e.g., a copper foil) that acts as an electromagnetic interference ("EMI") shield. The EMI shield layer 220 may be directly or indirectly connected to ground. The EMI shield layer 220 may be dimensionally configured to align with the traces 228 within the top and bottom electrical trace layers 212, 216; e.g., the EMI shield layer 220 may be configured to cover traces 228 within a trace layer 212, 216. The fold axis 208 shown in FIG. 13 illustrates the point at which the EMI shield layer 220 is folded over in the assembled sensor connector 200.

Figure 14:
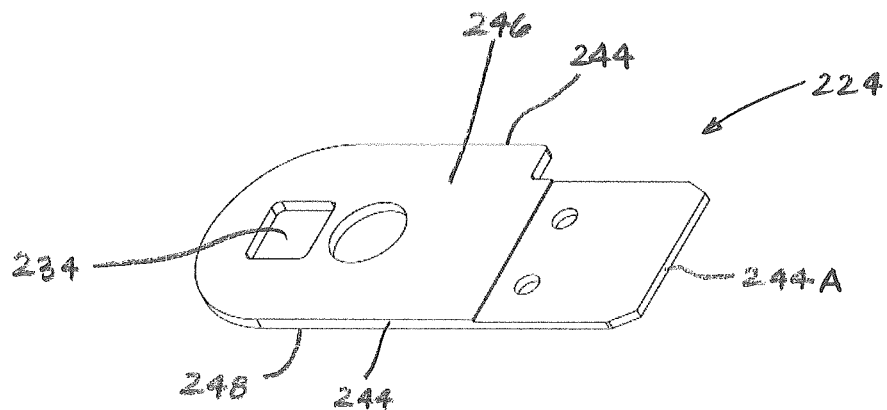
FIG. 14 is a perspective view of a stiffener panel embodiment.
Figure 14A:
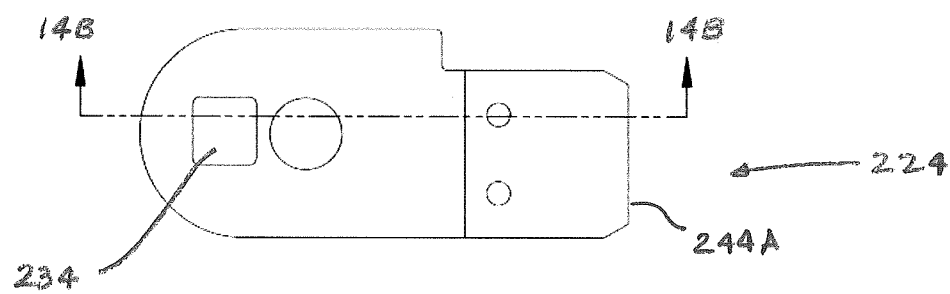
FIG. 14A is a planar view of the stiffener panel embodiment shown in FIG. 14.
Figure 14B:
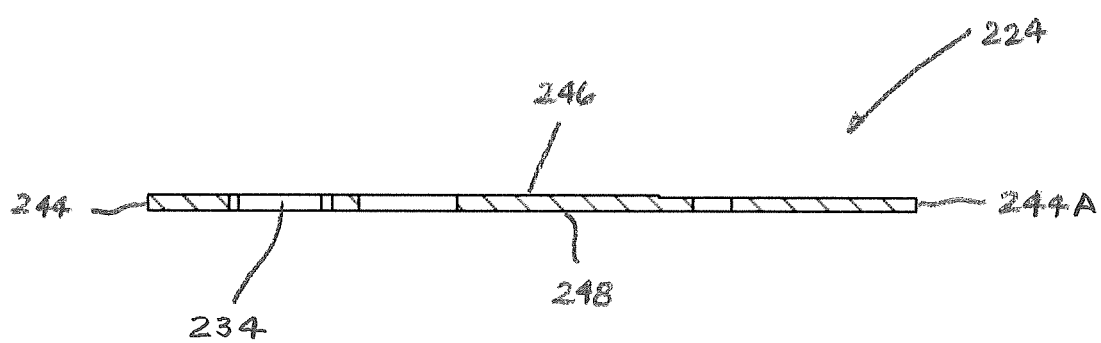
FIG. 14B is a sectional view of the stiffener panel embodiment shown in FIG. 14, which section is taken at line 14B-14B shown in FIG. 14A.

Now referring to FIGS. 14, 14A, and 14B, the stiffener panel 224 is configured to be a relatively rigid component that provides structural rigidity to the connector 200. The stiffener panel 224 includes a plurality of edges 244 (including an insertion edge 244A) that extend between a bottom side surface 246 and an opposing top side surface 248. The stiffener panel 224 may be made of various different materials or combinations of materials. For example, the stiffener panel 224 may consist of a polymer material (e.g., plastic) formed in a molding process. A molded plastic stiffener panel 224 is particularly useful for at least the reasons that it can be manufactured inexpensively, and can be manufactured to have a configuration with smooth surfaces and edges. The smooth edges of a molded plastic stiffener panel 224 greatly decreases the chance of undesirable wear with mating parts and the potential for creating debris from such wear (e.g., fiberglass particulates/fibers released from a fiberglass material such as FR-4). The rigidity provided by the stiffener panel 224 makes it easier for a user to insert the connector 200 into, or remove the connector 200 from, a mating connector element.

In some embodiments, a well 234 (e.g., a void having a width, length and thickness, which thickness extends between the inner and outer surfaces 246, 248 of the stiffener panel 224) is disposed in the bottom side surface 246 of the stiffener panel 224. Alternatively, an aperture may extend through the entire thickness of the stiffener panel 224; i.e., the aperture extends between the bottom side and top side surfaces 246, 248 of the stiffener panel 224 as shown in FIGS. 14, 14A, and 14B. The well or aperture (collectively referred to as "well 234" hereinafter to facilitate the present description) may be dimensionally configured to receive one or more components 236 (e.g., see FIGS. 5 and 6A) in communication with the flexible circuit 202; e.g., a memory chip (e.g., an EPROM), a resistor, a switch, etc. In FIGS. 14, 14A, and 14B the well 234 is shown in a rectangular configuration, but the connector 200 is not limited to a rectangular-shaped well 234. In some embodiments, the components 236 disposed within the well 216 may be operable to provide or store information (e.g., operational characteristics) relating to the sensor 12, which information may be communicated to, or accessible by, the base unit 14 (e.g., the processor portion of the base unit 14) to which the sensor 12 is connected; e.g., a component such as an EPROM may be programmed to provide information specific to that particular sensor 12, which specific information can be used in the operation of the sensor 12. Various techniques (e.g., a reflow solder technique) may be used to seat the component(s) 236 in the well 234. In some embodiments, potting compound or the like may be disposed within the well 234 to isolate the component(s) 236 and/or create a fluid barrier. The thickness of the well 234 permits the components 236 (each having a height that extends along the thickness direction of the stiffener panel 224) to be disposed within the connector 200 with limited impact on the overall thickness of the connector 200; e.g., if the height of the components 236 is equal to or less than the thickness of the well 234, the overall thickness of the connector 200 is not increased. In contrast, if the components 236 were simply placed on a surface 246, 248 of the stiffener panel 224 (e.g., if no well 234 was provided), the thickness of the connector 200 would be increased by the height of the components 236. Moreover, the well 234 provides a protective enclosure for the components 236.

FIG. 4 illustrates a sectional cut line (15-15) of the connector 200, and FIG. 15 illustrates a schematic diagram of the stack of layers within the connector 200 at the cut line. At this position, the schematic diagram shows the stack of layers in the following order: the top cover layer 210, the top electrical trace layer 212, the first electrically insulative layer 214, the bottom electrical trace layer 216, the second electrically insulative layer 218, the EMI shield layer 220, the stiffener panel 224, and the bottom cover layer 222. This diagrammatic cross-section illustrates an exemplary shielding arrangement relative to the traces used to conduct electrical signals to and from the light detectors. For example, the cross section shown in FIG. 15 shows a flexible circuit 202 embodiment for a sensor 12 that utilizes three separate light detectors (e.g., a near detector, a far detector, and a monitor detector, which monitor detector is positioned adjacent the light source 204). In this exemplary embodiment, the cross-sectional view reveals three similar trace arrangements (labeled as "I", "II", and "III") that each include a pair of traces 1528A, 528B; 1528C, 1528D; and 1528E, 1528F (all residing within the bottom electrical trace layer) for conducting electrical signals to and from a respective detector. Within each trace arrangement, each pair of traces (1528A, 528B; 1528C, 1528D; and 1528E, 1528F) are substantially enclosed by other traces electrically connected to function as EMI shielding. For example, in trace arrangement "I", traces 1628A and 1628B are disposed on opposite sides of traces 1528A and 1528B. Trace 1628A resides within the top electrical trace layer 212, and Trace 1628B resides within the EMI shield layer 220. Also in trace arrangement "I", traces 1628C and 1628D are disposed on opposite lateral sides of traces 1528A and 1528B. Traces 1628C and 1628D both reside within the bottom electrical trace layer 216. Similarly, in trace arrangement "II", traces 1728A and 1728B are disposed on opposite sides of traces 1528C and 1528D, and traces 1728C and 1728D are disposed on opposite lateral sides of traces 1528C and 1528D, and in trace arrangement "III", traces 1828A and 1828B are disposed on opposite sides of traces 1528E and 1528F, and traces 1828C and 1828D are disposed on opposite lateral sides of traces 1528E and 1528F. Traces 1928A-C (residing within the top electrical trace layer 212) and trace 1928D (residing within the bottom electrical trace layer 216) provide electrically conductive paths to the light detector(s) 204.

FIG. 4 illustrates a sectional cut line (16-16) of the connector 200, and FIG. 16 illustrates a schematic diagram of the stack of layers within the connector 200 at the cut line. At this position, a portion of the flexible circuit 202 is folded around the stiffener panel 224, and therefor resides on both sides of the stiffener panel 224. The schematic diagram shows the stack of layers in the following order: the top electrical trace layer 212, the first electrically insulative layer 214, the bottom electrical trace layer 216, the second electrically insulative layer 218, the EMI shield layer 220, the bottom cover layer 222, the stiffener panel 224, and then substantially the inverse: the bottom cover layer 222, the EMI shield layer 220, the second electrically insulative layer 218, the bottom electrical trace layer 216, the first electrically insulative layer 214, and the top electrical trace layer 212. At this position, the top cover layer 210 is not present, and traces within the top electrical trace layer 212 are exposed on both sides of the stiffener panel 224 so they can be electrically connected with a mating connector. FIG. 16 is provided to illustrate the folded circuit configuration having a central stiffener panel 224 with an EMI shield layer 220 disposed on both sides of the stiffener panel 224. FIG. 16 diagrammatically shows traces within the bottom electrical trace layer 216 and traces within the top electrical trace layer 212. The specific relative sizing and positioning of traces within the top and bottom electrical trace layers as shown in FIG. 16 is intended only to show the relative positioning of the layers themselves—not the specific traces within the layers. The present disclosure contemplates a variety of different trace configurations within either or both of the top and bottom electrical trace layers 212, 216, and the present disclosure is not therefore limited to any particular specific trace configuration within the top and bottom electrical trace layers 212, 216, at this position within the connector 200. Furthermore, the particular layers within the flexible circuit 202 represent one embodiment of a flexible circuit 202 and alternative flexible circuit configurations can be used in the folded over configuration. As can be seen in 9A and 10A, the top and bottom electrical trace layers may include apertures 250 (sometimes referred to as "vias") within which an electrical conductor can be disposed to create an electrical connection between certain traces within the top and bottom electrical trace layers; e.g., by plating or other electrically conductive material disposed within the vias 250.

Figure 17:
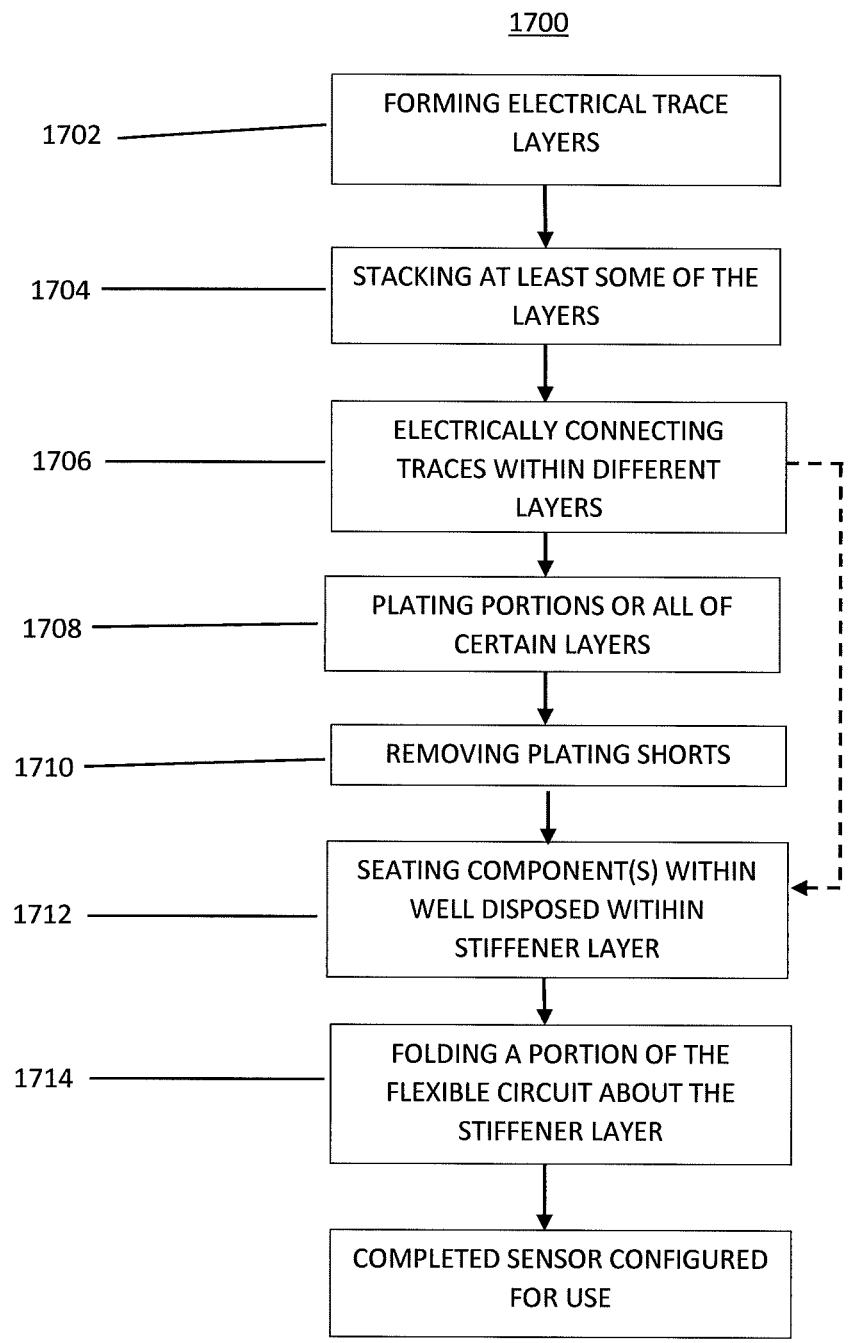
FIG. 17 illustrates a flowchart of a method for manufacturing a connector in accordance with aspects of this disclosure.

Referring now to FIG. 17, a flowchart of an exemplary method 1700 of manufacturing a sensor connector 200 is shown.

In block 1702, one or more electrical trace layers are formed. The traces are formed of at least one material as described above.

In block 1704, at least some of the layers (e.g., EMI shielding layers, trace layers, etc. —see descriptions above) are stacked.

In block 1706, some embodiments include the step of electrically connecting traces within different layers (e.g., connecting traces within the top electrical trace layer 212 to traces within the bottom electrical trace layer 216), which connections may be created using vias as described above.

In block 1708, portions (or all) of electrical circuit portions within the sensor may be plated.

In block 1710, for those embodiments that utilize plating, shorts installed to facilitate the plating process are removed.

Regarding block 1712, in those sensor embodiments that include a well (or aperture) disposed within the stiffener panel 224, the sensor component(s) may be seated within the well (or aperture). The component(s) may be seated by applying a reflow solder technique, and may potting material may be added to the well. The component(s) may be electrically connected to the flexible circuit 202. This step is optional and may be bypassed/eliminated in the connector 200 does not include a well 234 disposed within a stiffener panel 224.

In block 1714, the portion of the stacked layers (i.e., the flexible circuit 202) disposed on the side of the fold axis 208 opposite the portion of the sensor containing the light source(s) 204 and the light detector(s), is folded around the stiffener panel 224 and may be attached to the stiffener panel 224 (e.g., by an adhesive and/or mechanical fasteners).

In the folded over configuration (i.e., configured for use), as can be seen in FIGS. 2 and 4, the top cover layer 210 extends over a portion of the connector 12 and terminates at the beginning of a top-side exposed trace portion 238 of the connector 200. The exposed top-side trace portion 238 of the connector 200 (i.e., a portion of the top electrical trace layer 212) extends from the termination of the top cover layer 210 to the insertion edge 240 of the connector 200. In the particular non-limiting sensor embodiment described above, exposed traces 228 within the top-side exposed trace portion 238 provide the electrical connection means for connecting the sensor components (e.g., light source(s) 204, etc.) to the mating connector with which the present connector 200 may be coupled.

On the bottom-side of the present connector 200 in the folded over configuration (i.e., configured for use) as can be seen in FIGS. 3 and 5, the separated segment 226 of the top cover layer 210 (independent of the remainder of the top cover layer 210) is attached to and forms a portion of the flexible circuit 202 folded around the stiffener panel 224. On one side of the top cover layer segment 226 (i.e., on the side closest to the portion of the sensor 12 containing the light source(s) 204 and light detector(s) 206) a portion of the stiffener panel 224 is exposed. In some embodiments that include a well 234 disposed within the stiffener panel 224, the well 234 may be visible in the finally assembled sensor 12. On the opposite side of the top cover layer segment 226, the exposed bottom-side trace portion 242 (i.e., a portion of the top electrical trace layer 212) extends from the top cover layer segment 226 to the insertion edge 240 of the connector 200. In the particular non-limiting sensor embodiment described above, exposed traces 228 within the bottom-side exposed trace portion 242 provide the electrical connection means for connecting sensor components (e.g., light detector(s) 206) to the mating connector with which the present connector 200 may be coupled.

The blocks of the method 1700 are illustrative. The operations associated therewith may be performed in an order or sequence that is different from what is shown in FIG. 17. In some embodiments, one or more of the blocks (or one or more portions thereof) may be optional. In some embodiments, one or more additional blocks/operations not shown may be included.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional in accordance with aspects of the disclosure.

What is claimed is:

1. An oximetry sensor assembly connector, comprising:
   a flexible circuit having a plurality of layers including at least one electrical trace layer and at least one electromagnetic interference (EMI) shield layer; and
   a stiffener panel having a first side surface, a second side surface, and an insertion edge, wherein the second side surface is opposite the first side surface, and the insertion edge extends between the first side surface and the second side surface;
   wherein the flexible circuit includes a first segment and a second segment, and one or more of the plurality of layers are disposed within the first segment and the second segment; and
   wherein the flexible circuit is folded such that the first segment is contiguous with the first side surface of the stiffener panel, and the second segment is contiguous with the second side surface of the stiffener panel, and the insertion edge is disposed at the fold of the flexible circuit; and
   wherein the first segment of the flexible circuit includes a first exposed portion adjacent the insertion edge of the stiffener panel, and a first covered portion, and the second segment of the flexible circuit includes a second exposed portion adjacent the insertion edge of the stiffener panel, and a second covered portion; and
   wherein the plurality of layers within the flexible circuit includes a first electrically conductive layer and the first electrically conductive layer is exposed as the outermost layer in both the first exposed portion and in the second exposed portion; and
   wherein within the first exposed portion, the plurality of layers of the flexible circuit includes in stacked order in a direction toward the stiffener panel, the first electrically conductive layer, a first electrically insulative layer, a second electrically conductive layer, a second electrically insulative layer, the EMI shield layer, and a cover layer, which cover layer is in contact with the first side surface of the stiffener panel.

2. The connector of claim 1, wherein within the second exposed portion, the plurality of layers of the flexible circuit includes in stacked order in a direction toward the stiffener panel, the first electrically conductive layer, the first electrically insulative layer, the second electrically conductive layer, the second electrically insulative layer, the EMI shield layer, and the cover layer, which cover layer is in contact with the second side surface of the stiffener panel.

3. The connector of claim 2 wherein within the first covered portion of the first segment, the plurality of layers of the flexible circuit further includes a second cover layer in contact with the first electrically conductive layer, and within the second covered portion of the second segment, the plurality of layers of the flexible circuit further includes the second cover layer in contact with the first electrically conductive layer.

4. The connector of claim 1, wherein the first electrically conductive layer includes one or more light source traces configured to conduct electrical signals between one or more light sources within the sensor assembly and one or both of the first and second exposed portions, and one or more EMI shield traces.

5. The connector of claim 4, wherein the second electrically conductive layer includes one or more detector traces configured to conduct electrical signals between one or more light detectors within the sensor assembly and one or both of the first and second exposed portions, and one or more EMI shield traces.

6. The connector of claim 5, wherein within the flexible circuit, one or more of the EMI shield traces in the second electrically conductive layer are aligned with the one or more light source traces within the first electrically conductive layer, and one or more of the EMI shield traces in the first electrically conductive layer are aligned with the one or more detector traces within the second electrically conductive layer.

7. The connector of claim 1, wherein the stiffener panel includes a well extending between the first side surface and the second side surface, and further including one or more electrical components disposed within the well and in connection with the flexible circuit.

8. An oximetry sensor assembly, comprising:
   at least one light source;
   at least one light detector;
   a flexible circuit having a plurality of layers including at least one electrical trace layer and at least one electromagnetic interference (EMI) shield layer; and a connector that includes a stiffener panel having a first side surface, a second side surface, and an insertion edge, wherein the second side surface is opposite the first side surface, and the insertion edge extends between the first side surface and the second side surface;

wherein the flexible circuit extends between the light source and light detector proximate a first end, and the connector at a second end opposite the first end;

wherein the flexible circuit includes a first segment and a second segment, and one or more of the plurality of layers are disposed within the first segment and the second segment; and wherein the flexible circuit is folded such that the first segment is contiguous with the first side surface of the stiffener panel, and the second segment is contiguous with the second side surface of the stiffener panel, and the insertion edge is disposed at the fold of the flexible circuit; and wherein the first segment of the flexible circuit includes a first exposed portion adjacent the insertion edge of the stiffener panel, and a first covered portion, and the second segment of the flexible circuit includes a second exposed portion adjacent the insertion edge of the stiffener panel, and a second covered portion; and wherein the plurality of layers within the flexible circuit includes a first electrically conductive layer and the first electrically conductive layer is exposed as the outermost layer in both the first exposed portion and in the second exposed portion; and wherein within the first exposed portion, the plurality of layers of the flexible circuit includes in stacked order in a direction toward the stiffener panel, the first electrically conductive layer, a first electrically insulative layer, a second electrically conductive layer, a second electrically insulative layer, the EMI shield layer, and a cover layer, which cover layer is in contact with the first side surface of the stiffener panel.

9. The sensor assembly of claim 8, wherein within the second exposed portion, the plurality of layers of the flexible circuit includes in stacked order in a direction toward the stiffener panel, the first electrically conductive layer, the first electrically insulative layer, the second electrically conductive layer, the second electrically insulative layer, the EMI shield layer, and the cover layer, which cover layer is in contact with the second side surface of the stiffener panel.

10. The sensor assembly of claim 8, wherein the first electrically conductive layer includes one or more light source traces configured to conduct electrical signals between one or more light sources within the sensor assembly and one or both of the first and second exposed portion, and one or more EMI shield traces.

11. The sensor assembly of claim 10, wherein the second electrically conductive layer includes one or more detector traces configured to conduct electrical signals between one or more light detectors within the sensor assembly and one or both of the first and second exposed portions, and one or more EMI shield traces.

12. The sensor assembly of claim 11, wherein within the flexible circuit, one or more of the EMI shield traces in the second electrically conductive layer are aligned with the one or more light source traces within the first electrically conductive layer, and one or more of the EMI shield traces in the first electrically conductive layer are aligned with the one or more detector traces within the second electrically conductive layer.

* * * * *